(12) United States Patent
Karmon et al.

(10) Patent No.: US 9,636,442 B2
(45) Date of Patent: May 2, 2017

(54) PRESSURE ACTUATED SINGLE-LUMEN BLOOD PUMPING DEVICE

(71) Applicant: PULSECATH B.V., Amsterdam (NL)

(72) Inventors: Yoram Karmon, Petach Tikvah (IL); Jan-Paul Van Loon, Amsterdam (NL)

(73) Assignee: PULSECATH B.V., Amsterdam (NL)

( * ) Notice: Subject to any disclaimer, the term of this patent is extended or adjusted under 35 U.S.C. 154(b) by 0 days.

(21) Appl. No.: 13/743,510

(22) Filed: Jan. 17, 2013

(65) Prior Publication Data

US 2013/0184514 A1 Jul. 18, 2013

Related U.S. Application Data

(60) Provisional application No. 61/587,174, filed on Jan. 17, 2012.

(30) Foreign Application Priority Data

Jan. 17, 2012 (EP) .................................... 12151442

(51) Int. Cl.
*A61N 1/362* (2006.01)
*A61M 1/10* (2006.01)

(52) U.S. Cl.
CPC ........ *A61M 1/1037* (2013.01); *A61M 1/1046* (2013.01); *A61M 1/101* (2013.01); *A61M 1/106* (2013.01)

(58) Field of Classification Search
CPC .... A61M 1/101; A61M 1/106; A61M 1/1037; A61M 1/1046

USPC .............. 623/3.21; 600/16; 422/44; 604/6.1, 604/6.11, 43

See application file for complete search history.

(56) References Cited

U.S. PATENT DOCUMENTS

| | | | |
|---|---|---|---|
| 3,553,736 A | | 1/1971 | Kantrowitz |
| 4,552,552 A | | 11/1985 | Polaschegg et al. |
| 4,985,014 A | * | 1/1991 | Orejola ........................... 600/16 |
| 5,089,016 A | | 2/1992 | Millner et al. |
| 6,007,479 A | | 12/1999 | Rottenberg et al. |
| 6,132,364 A | | 10/2000 | Rottenberg et al. |
| 6,398,714 B1 | | 6/2002 | Verkerke et al. |

(Continued)

FOREIGN PATENT DOCUMENTS

| | | |
|---|---|---|
| EP | 1072278 | 1/2001 |
| GB | 1242418 A | 8/1971 |

(Continued)

*Primary Examiner* — Lindsey G. Wehrheim
(74) *Attorney, Agent, or Firm* — Pearne & Gordon LLP

(57) ABSTRACT

A pressure actuated single-lumen blood pumping device has a housing (4) having a wall (19) bounding a pressure transfer chamber (11; 411). The housing (4) bounds a pressure transfer port (9) for connection to a pressure source, the pressure transfer port (9) communicating with the pressure transfer chamber (11; 411) for alternatingly transferring over pressure and under pressure from the pressure source to the pressure transfer chamber (11; 411). A flexible tubular membrane (2; 102; 202; 302; 402) is arranged in the pressure transfer chamber (11; 411). A blood transfer conduit (3; 103; 203; 303; 403) passes through the wall (19) bounding the pressure transfer chamber (11; 411) and the blood transfer conduit (3; 103; 203; 303; 403) connects to opposite ends (5, 6; 105; 405, 406) of the flexible tubular membrane (2; 102; 202; 302; 402).

18 Claims, 3 Drawing Sheets

(56) References Cited

U.S. PATENT DOCUMENTS

| | | |
|---|---|---|
| 6,974,409 B2 | 12/2005 | Verkerke et al. |
| 7,217,236 B2 * | 5/2007 | Calderon et al. ............ 600/16 |
| 8,376,927 B2 * | 2/2013 | Tovar Lopez ............ 600/16 |
| 2002/0123661 A1 | 9/2002 | Verkerke et al. |
| 2006/0206048 A1 * | 9/2006 | Loggie ............ 604/6.16 |

FOREIGN PATENT DOCUMENTS

| | | |
|---|---|---|
| WO | 00/03754 | 1/2000 |
| WO | 2005021078 | 3/2005 |
| WO | 2008102015 A1 | 8/2008 |

* cited by examiner

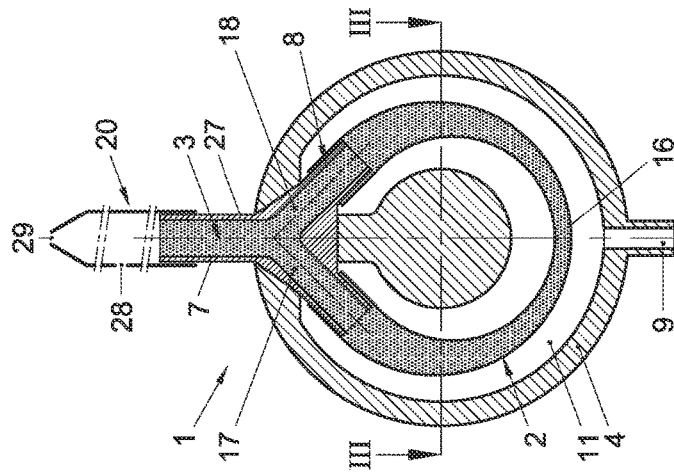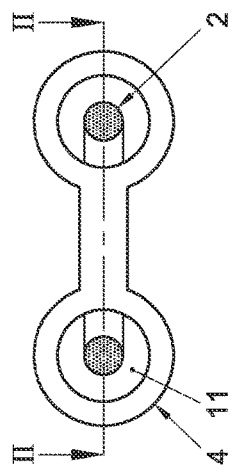
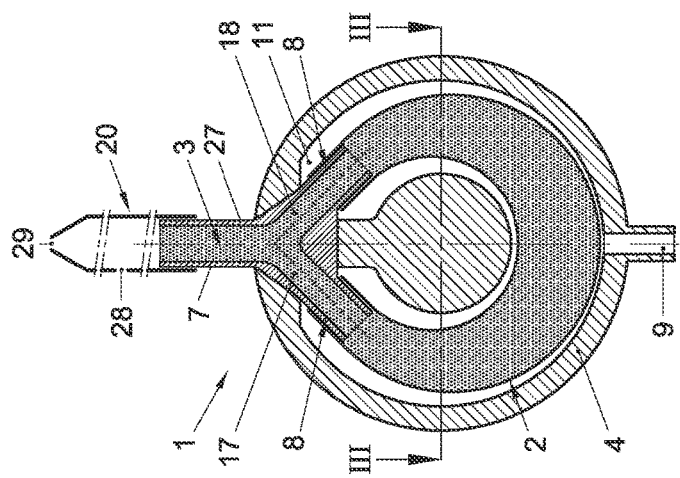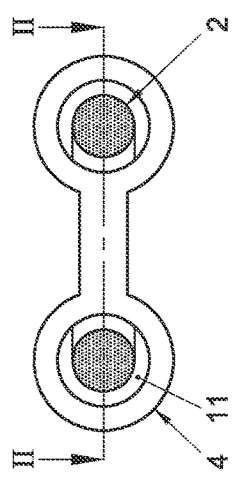
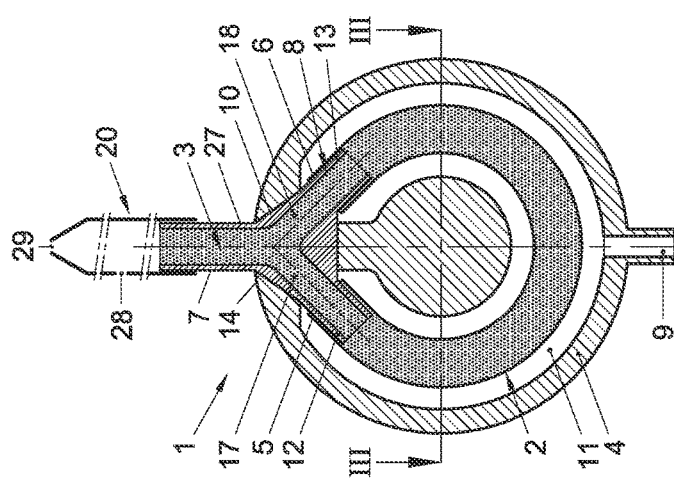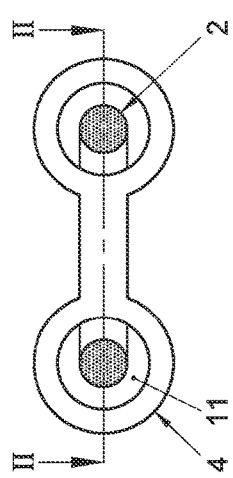

PRESSURE ACTUATED SINGLE-LUMEN BLOOD PUMPING DEVICE

TECHNICAL FIELD

The invention relates to a pressure actuated single-lumen blood pumping device. Such a device can for instance be used for pumping blood in a circulatory assist system.

BACKGROUND OF THE INVENTION

Membrane pumps for pumping blood are well known in the art. For instance from European patent 1 072 278 and WO-A1-2005/021078 single-lumen membrane blood pumps are known which include a displacement device in the form of a generally rigid housing bounding an inner space divided in two compartments by a flexible membrane. In operation, one compartment contains blood and the other compartment contains a gas (e.g. ambient air). This known displacement device has a socket to which a single-lumen catheter is connected. The single-lumen catheter has an outlet passage at a distal end thereof and inlet passages proximally spaced from the outlet for transporting blood through the catheter from the inlet to the outlet over the distance between the inlet and the outlet. The gas compartment has an opening for connection to a conduit communicating with a drive unit. The drive unit generates under pressure and overpressure (relative to the current pressure in the lumen and the blood compartment), thereby alternatingly removing gas from the gas compartment and pressing gas into the gas compartment, respectively. During the aspiration phase, the under pressure draws the membrane towards a first side of the shell, aspiring blood via the inlet passages and also, to some extent, via the outlet passage of the single-lumen catheter into the membrane pump. This is followed by the ejection phase, when the pressure pushes the membrane back from the first side of the shell towards a second side of the shell opposite of the first side, thereby expelling blood out of the shell and into the catheter lumen. When blood is expelled, the orientation of the flow past the inlet opening causes no or relatively little of the blood to flow out via the inlet opening, so that alternatingly aspiring and ejecting blood in a sequential mode, results in a net pumping effect. In such a single-lumen pump, in which blood flows into and out of a compartment, the residence time of some of the blood in the blood compartment can become quite long which entails a risk of clot formation.

From WO 00/03754 a membrane pump is known which also includes an outer shell with a membrane dividing the inner space in a blood compartment and a gas compartment. In this membrane pump two sockets, each containing a one-way valve, allow blood to flow in and out of the blood compartment and each communicate with a lumen of a double lumen portion of the catheter, the lumen joining into a single-lumen in a position spaced from the sockets. The sockets are each provided with a one-way valve, the valves being arranged such that one of the sockets allows blood to flow into the membrane pump only while the other socket allows blood to flow out of the blood compartment only. According to this document, turbulence in the blood flow and exposure of blood components to mechanical stress are minimized because the blood path is at least partially circulating, so stagnation of the blood flow is prevented. However, at the valves, local stagnation of the flow, turbulence and exposure of blood components to mechanical stress can be expected.

In both of the above-discussed membrane pumps, the membrane is mounted in-between two shell parts forming the outer shell. As blood has the ability to clot easily, all edges and sharp corners need to be rounded in order to avoid blood damage and clotting. This rounding is performed by smoothening the corners and edges. The transition from the membrane to the rigid outer shell is especially vulnerable for clotting. This requires several coating processes to make sure the transition is completely smoothened. In addition, the transitions of the top shell to the socket/sockets need to be smoothened. For these reasons, the manufacturing of membrane pumps requires several time consuming steps. This makes membrane pumps relatively expensive, which is particularly disadvantageous because sterility requirements impose that cardiac assist membrane pumps are used as disposable items only.

SUMMARY OF THE INVENTION

It is an object of the invention to provide a simple and reliable pressure actuated single-lumen blood pumping device which can be manufactured at reduced costs and of which the use entails less risk of blood clotting.

According to the invention this object is achieved by providing a pressure actuated single-lumen blood pumping device including:

a housing having a wall bounding a pressure transfer chamber, the housing comprising a pressure transfer port for connection to a pressure source, the pressure transfer port communicating with the pressure transfer chamber for alternatingly transferring overpressure and under pressure from the pressure source to the pressure transfer chamber;

a flexible tubular membrane in the pressure transfer chamber, the flexible tubular membrane having opposite ends and bounding a blood chamber; and a blood transfer conduit passing through the wall bounding the pressure transfer chamber and having a single-lumen portion branching into lumen branches;

wherein the blood transfer conduit connects to the opposite ends of the flexible tubular membrane; and wherein the blood transfer conduit has a second proximal end at an end of a second one of the lumen branches, a first one of the proximal ends being at an end of a first one of the lumen branches and coupled to a first one of the ends of the elastic tubular membrane and the second proximal end being coupled to the second end of the elastic tubular membrane.

By using a flexible tubular membrane in the pressure transfer chamber as the boundary between air or other driving fluid and blood to be displaced, a blood pumping device without edges and sharp corners in the blood chamber can be obtained in a simple manner. In this way, a pumping device internally shaped to avoid blood damage and clotting can be manufactured at lower costs. Since both ends of the tubular membrane are connect to the single lumen, blood can flow in and out of the tubular membrane at both opposite ends, so none of these ends constitutes a dead end in which unfavourably long blood residence times could occur.

Arrangements making the pumping device specifically suitable for connection to and communication with a single-lumen may for instance comprise that at least a distal end portion of the blood transfer conduit is in the form of a single-lumen, that a single socket bounding the distal end portion of the blood transfer conduit is provided and/or that the blood compartment has a single port or single blood transfer conduit portion via which blood must pass to flow into or out of the blood chamber.

Preferably, the flexible tubular membrane has a curved shape. This allows interconnecting the opposite ends of the tubular membrane to the same lumen of the tube with little curvature in the flow path, so that a smooth flow towards and away from the blood chamber can be achieved.

A particularly efficient way of establishing communication between the blood chamber and the lumen of the tube is achieved because, firstly, the blood transfer conduit includes a single-lumen portion branching into lumen branches each coupled to one of the opposite ends of the flexible tubular membrane.

In one elaboration, the single-lumen portion of the blood transfer conduit is in line with a centre-line of the housing and the lumen branches of the blood transfer conduit are oriented obliquely and located mirror symmetrical relative to the single-lumen portion of the blood transfer conduit. Thus, the curvature in the blood transfer conduit between the lumen of the catheter and the blood chamber, and accordingly flow resistance and shear and/or turbulence in the flow, is evenly distributed between the two branches connected to the blood chamber, so the maximum resistance is relatively low.

However, to promote net circulation of blood through the blood chamber in the flexible tubular membrane successive pumping cycles, it is preferred that the single-lumen portion of the blood transfer conduit is in line with a first one of the lumen branches and the second one of the lumen branches joins the single-lumen portion and the first one of the lumen branches in an orientation with a directional component transverse to the single-lumen portion and the first one of the lumen branches. This causes a pressure drop over the connection of the second branch to the first branch and the single-lumen portion from the blood chamber towards the single-lumen portion of the blood transfer conduit during blood outflow, to be supported by a pressure reduction due to flow from the first lumen branch to the single-lumen portion while during inflow the reduction of the pressure due to flow from the single-lumen portion to the first lumen branch in line therewith counteracts a pressure drop from the single-lumen portion to the second lumen branch. Over a succession of pressure alternation cycles, this results in a net inflow of blood into the blood chamber via the first lumen branch and a net outflow of blood from the blood chamber via the second lumen branch. Accordingly a net blood circulation through the blood chamber from the first lumen branch to the second lumen branch is obtained, so that the amount of blood that stays in the blood chamber for a long time is at least reduced. For instance the $95^{th}$ percentile residence time is substantially lowered.

Net blood circulation through the flexible tubular membrane can be further enhanced by providing that the single-lumen portion of the blood transfer conduit is in line with the first socket.

For reducing the volume of blood moving back and forth, a compact construction with short flow lines is advantageous. For this purpose, it is preferred that centre-lines of the first socket and the second socket enclose an angle of approximately 90°.

By providing that the second one of the lumen branches comprises a first section branching off from the single-lumen portion at an obtuse angle and a second section spaced from the single-lumen portion, that is connected to the flexible tubular membrane and oriented more transversely to the single-lumen portion than the first section, outflow from the blood chamber via the second lumen branch and accordingly net circulation through the blood chamber is further enhanced.

Outflow from the blood chamber via the second lumen branch and accordingly net circulation through the blood chamber can be yet further enhanced by providing that the single-lumen portion has an inner cross-section substantially larger than each of the inner cross-sections of the first and second lumen branches, for instance equal to the sum of the inner cross-sections of the first and second lumen branches.

The relation between inflow in the first lumen and second lumen can further be influenced by reducing the inner cross section of one of the lumen, for instance by providing that the first section of the second lumen branch has a smaller inner cross-section than an inner cross-section of the second section of the second lumen branch.

For an efficient blood transfer flow into and out of the chamber, it is preferred that at least a single-lumen portion of the blood transfer conduit is arranged tangential to the flexible tubular membrane, which constitutes a sector of a circular ring-shape. This causes the single-lumen portion of the blood transfer conduit to be generally in line with an adjacent section of the ring-sector shaped blood chamber.

It can furthermore be provided that the curved flexible tubular membrane has a ring-shaped portion and a tubular end portion arranged tangential to said ring-shaped portion and connected to a socket bounding the proximal end of the blood transfer conduit. Thus, manufacturing costs can be further reduced, because a single end connected to a socket bounding a proximal end of the blood transfer conduit suffices and the blood transfer conduit may be a single-lumen conduit over its entire length. Net blood circulation through the blood chamber is nevertheless achieved due to the tangential orientation of the tubular end portion relative to the ring-shaped portion. The directional effect of inflow is stronger than that of outflow, so that a net circulation in a sense converging with the tubular end portion is achieved.

For an effective pressure transfer from the pressure transfer chamber to the blood in the flexible tubular membrane, it is essential that the pressure transfer chamber and the flexible tubular membrane are both curved around a common central area. Thus, the free space around the flexible tubular membrane in which gas can expand and be compressed is kept small.

Also for an effective pressure transfer, it is preferred that the housing is hermetically sealed.

If the flexible tubular membrane is of an elastic material, a relatively large displacement volume per pumping stroke can be achieved while avoiding or reducing the occurrence of areas inside the tubular membrane where opposite wall surfaces contact each other or approach each other very closely. This is advantageous for avoiding squeezing of blood and accordingly limiting shear gradients in the blood flow inside the tubular membrane.

Further objects, features, effects, advantages and details of the invention are described with reference to examples shown in the drawings.

BRIEF DESCRIPTION OF THE DRAWINGS

FIGS. 2A-2C are schematic cross-sectional top views, along the lines II-II in FIGS. 3A-3C respectively, of the device shown in FIG. 1 in three successive stages of a pumping cycle;

FIGS. 3A-3C are schematic cross-sectional side views, along the lines III-III in FIGS. 2A-2C respectively, corresponding to the top views as shown in FIGS. 2A-2C, respectively.

DETAILED DESCRIPTION

Figure 1:
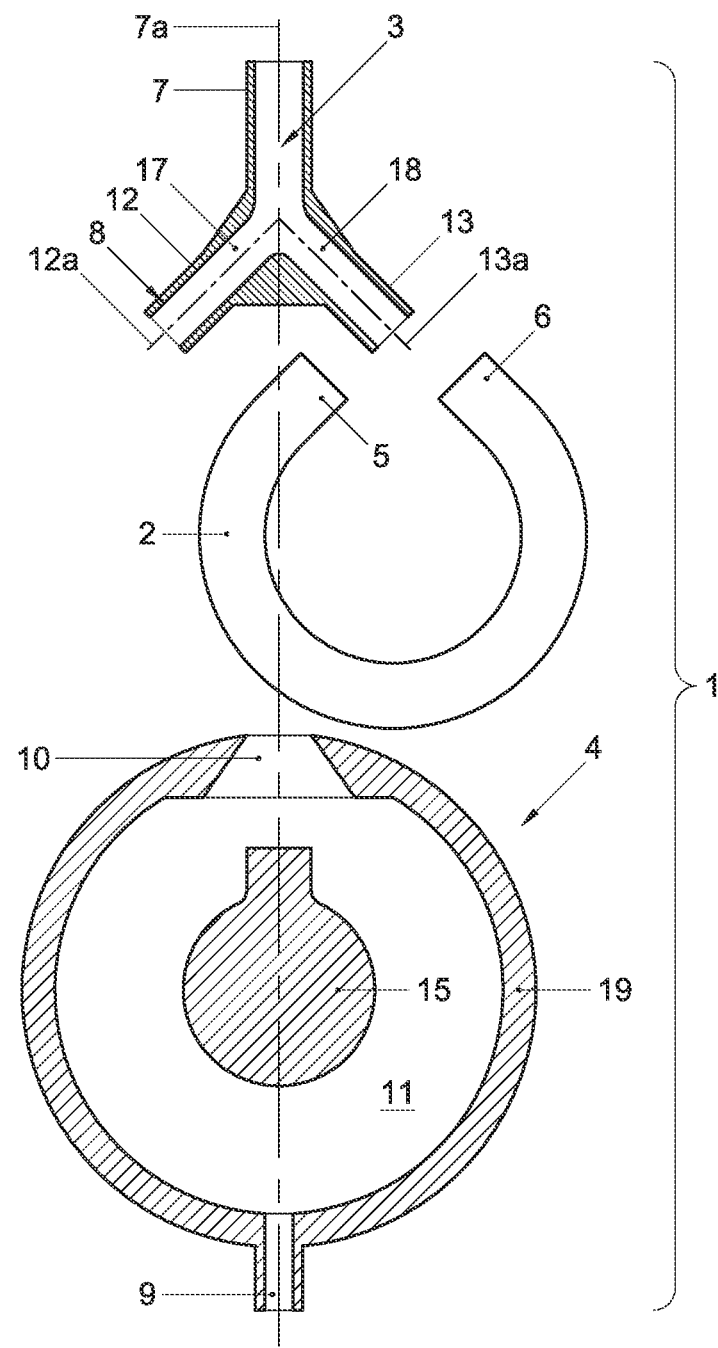
FIG. 1 is a schematic, partly cross-sectional exploded view of an example of a pressure actuated single-lumen pumping device according to the invention.

In FIG. 1 three main parts of an example of a pressure actuated single-lumen blood pumping device 1 are shown: firstly, a generally rigid housing 4 bounding a pressure transfer chamber 11; secondly, an flexible tubular membrane 2 to be fitted in the pressure transfer chamber 11; and thirdly, a fitting 8 bounding a blood transfer conduit 3.

As can be seen in FIG. 1, in particular in conjunction with FIGS. 2A-2C and 3A-3C, the flexible tubular membrane 2 has a first end 5 and a second end 6. The blood transfer conduit 3 includes a single-lumen portion 7 and first and second lumen branches 17, 18. The rigid housing 4 has a pressure transfer port 9 including a socket for connection to a pressure source for alternatingly applying overpressure and under pressure (relative to the pressure in the tubular membrane and in a lumen of a tube communicating therewith) to the pressure transfer chamber 11. As a result, the flexible tubular membrane 2 is alternatingly expanded and compressed, thereby causing blood to flow into and out of a blood chamber bounded by the flexible tubular membrane 2. The overpressure and under pressure are applied by alternatingly driving a driving fluid into the pressure transfer chamber 11 and drawing fluid out of the pressure transfer chamber 11, via the pressure transfer port 9. The driving fluid may be a gas such as ambient air, but may also be a liquid, for instance an isotonic solution. In particular if a liquid is used, the driving fluid may also be used for controlling or at least warming or cooling the temperature of the blood in the flexible tubular membrane 2. The housing 4 further has a single opening 10 in which the fitting 8 bounding the blood transfer conduit 3 is sealingly fitted. The pressure source can be any kind of source of alternatingly varying pressure. Since such pressure sources are generally known in the art, for instance in the form of an Intra-Aortic Balloon Pump driver, a description thereof is not included.

As can be seen in FIGS. 2A-2C and 3A-3C, the pressure transfer chamber 11 in the housing 4 is of a generally annular shape apart from an interruption at a common midplane of the fitting 8 and the housing 4.

In assembled state, the fitting 8 bounding the blood transfer conduit 3 is sealingly fitted in the passage in the housing 4. A portion of the fitting 8 bounding the single-lumen portion 7 constitutes a socket 27 projecting outwardly from the housing 4. A tube in the form of a catheter 20 is connected to the projecting socket 27. The catheter 20 has a single-lumen for displacing blood from an inlet 28 to an outlet 29 distally spaced from the inlet 28. Such catheters are known from European patent 1 072 278 and international patent application WO2005/021078 to which reference is made. The catheter 20 is regarded as a single-lumen catheter in the sense that it has a single primary lumen for displacement of blood with blood inlet and outlet ports. However, other, secondary lumen for other purposes such as the administration of medicaments or a contrast medium may be provided. Instead of a catheter, a tube that may communicate with further circuitry with or without valves can be connected to the socket 27.

In assembled and operational state, the housing 4 is hermetically sealed, so that overpressure and under pressure, respectively, can efficiently be applied via the pressure transfer port 9 and the flexible tubular membrane 2 onto the blood in the blood chamber. The flexible tubular membrane 2 has a curved shape generally coaxial with the curvature of the generally tube-shaped pressure transfer chamber 11 bounded by the housing 4. The flexible tubular membrane 2 may have been formed into the curved shape, for instance by plastic deformation while arranged over a core that is bent, or be flexibly and/or elastically bent into that curved shape. A combination of the curvature being partially pre-formed and partially obtained by bending during installation is also possible. The proximal end of the blood transfer conduit 3 is formed by two sockets 12, 13 bounding lumen branches 17, 18 branching off from a single-lumen portion 7 of the blood transfer conduit 3. A first end 5 and a second end 6 of the flexible tubular membrane 2 are mounted to the sockets 12 and 13 respectively, such that hermetically sealed connections are obtained. In the embodiment shown in FIGS. 1-3, the first socket 12 is separate from the second socket 13.

A particular advantage of providing the membrane in tubular form, is that it can be manufactured in a simple manner, for instance by extrusion or dipping over a cylindrical mandrel. Yet, because both opposite ends of the membrane are open and are each connected to a branch of the blood transfer conduit, a dead end in which too long blood residence times can easily occur is avoided. The material from which the tubular membrane is made may for instance be Polyurethane or Silicone material, preferably dimensioned to stretch less than 5 or 10% during pumping in normal use.

As is best seen in FIG. 1, the first lumen branch 17 has a first central axis 17a and the second lumen branch 18 has a second central axis 18a. The sockets 12 and 13 are coaxial with the corresponding first and second central axes 17a and, respectively 18a. In the embodiment shown in FIGS. 1-3, the first and second central axes 17a and 18a are mirror symmetrically arranged with regard to a central axis 7a of the single-lumen portion 7, which is in line with a symmetry plane of the housing 4. In the embodiment shown, the first and second central axes 17a and 18a of the lumen branches 17, 18 and the sockets 12, 13 enclose an angle of approximately 90°, so the curvature of the flexible tubular membrane 2 extends over approximately 270°, which allows for easy mounting while the angles over which the lumen branches 17, 18 are deflected relative to the single-lumen portion 7 of the blood transfer conduit 3 are at approximately a relatively modest 45° which is favourable for avoiding flow resistance and turbulence.

In FIGS. 2A-2C and 3A-3C the pressure actuated single-lumen pumping device 1 is shown during three phases of a pumping cycle when the pumping device 1 is in operation assisting the heart of a patient. In FIGS. 2A and 3A the pressure source is in an intermediate state, while in transition between a condition of under pressure (FIGS. 2B and 3) and a condition of overpressure (FIGS. 2C and 3C). In this neutral state, the flexible tubular membrane 2 is in its least deformed condition. It is however also possible to provide that the least deformed condition is closer to or at the largest or smallest internal volume state.

If the pressure applied via the port 9 decreases by causing the driving fluid, in the present example ambient air, to flow out of the pressure transfer chamber 11, the flexible tubular member 2 is caused to expand as is illustrated by FIGS. 2B and 3B. As the flexible tubular member 2 is caused to expand, blood is drawn from the catheter 20 through the blood transfer conduit 3 into the flexible tubular membrane 2. Subsequently the pressure source presses air via the port 9 into the pressure transfer chamber 11 such that an over pressure is generated in the pressure transfer chamber 11 and applied to the flexible tubular membrane 2. This causes the flexible tubular member 2 to shrink again to the neutral state shown in FIGS. 2A and 3A and subsequently on to the collapsed state shown in FIGS. 2C and 3C. During this transition, blood is pressed out of the flexible tubular membrane 2 and, via the blood transfer conduit 3, into the single-lumen catheter 20.

A central portion 15 of the housing 4 bounds an inside contour of the pressure transfer chamber 11 and keeps the flexible tubular membrane 2 in the collapsed condition shown in FIGS. 2C and 3C from being displaced out of its generally horseshoe shaped curvature during repeated pumping cycles, so that extreme deformations and the formation of dead end spaces where total residence times of blood could become too long and where blood particles could be exposed to large loads, is avoided, even if the flexible tubular membrane 2 is emptied virtually completely after each maximum overpressure.

Because in particular the portion of the flexible tubular membrane 2 centrally between its two ends 5, 6 can be emptied virtually completely, it is counteracted that the same blood volumes are moved back and forth for a very large number of times, so the maximum residence time of blood is kept relatively low.

In the example shown in FIGS. 2 and 3 a portion 16 (vide FIG. 2C) of the flexible tubular membrane 2 opposite the inlet/outlet passage 10 is attached to the housing 4 to avoid that the flexible tubular membrane 2 blocks the port 9 during the evacuation of air from the pressure transfer chamber 11. For this purpose it may also be provided that an air permeable support structure and/or texture is provided at least in the vicinity of the pressure transfer port 9 and more preferably at each part of the inner surface of the pressure transfer chamber that may be contacted by the flexible tubular membrane 2.

For reducing the maximum residence time of blood, it is furthermore advantageous to promote a net circulation of the blood through the flexible tubular membrane, for instance by providing members such as a one way valve or passively pivotable paddles facilitating flow in one direction and inhibiting flow in the opposite direction. Thus the maximum residence time of blood in the pumping device 1 can be further reduced.

Figure 4:
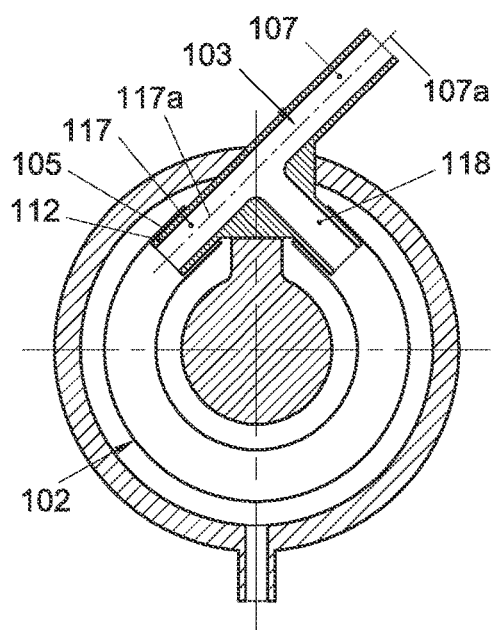
FIGS. 4-7 are schematic cross-sectional top views of four other examples of a pumping device according to the invention.
Figure 5:
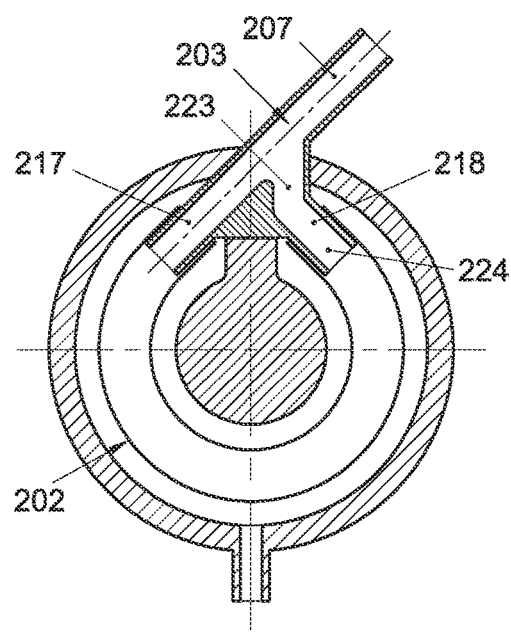
Figure 6:
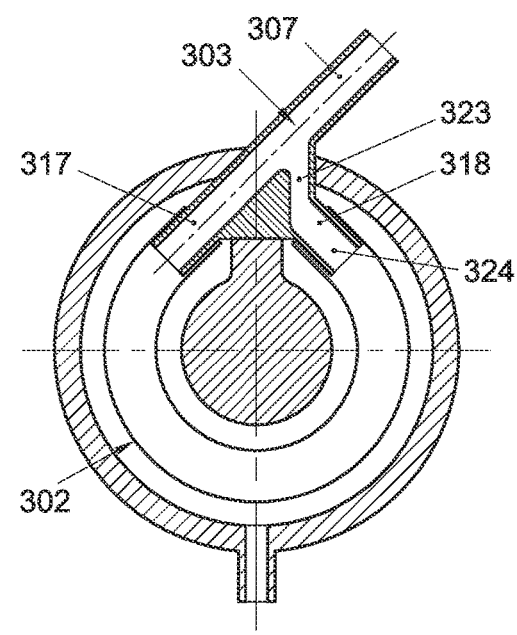

In the examples of a pressure actuated single-lumen pumping device shown in FIGS. 4-6 the blood transfer conduit used is a so-called T-connector.

In the example shown in FIG. 4, the single lumen portion 107 of the blood transfer conduit 103 has a centre line 107a in line with a centre line 117a of a first lumen branch 117 of the blood transfer conduit 103 while, in contrast, the second lumen branch 118 is oriented transversely to the centre line 107a of the single lumen portion 107. The centre line 107a of the single lumen portion 107 of the blood transfer conduit 103 is also aligned with the first socket 112 bounding a proximal end of the first lumen branch 117 of the blood transfer conduit 103 and accordingly with the first end 105 of the flexible tubular membrane 102. Furthermore, the centre lines 107a and 117a of both the single lumen portion 107 and the first lumen branch 117 of the blood transfer conduit 103 are arranged tangentially to the curve formed by the flexible tubular membrane 102. All these features, each by themselves as well as in combination, enhance the inflow of blood during the expansion stroke as the flexible tubular membrane 102 is expanded and accordingly enhance a net circulation in the sense of outflow out of the first lumen branch 117. As a result, during the aspiration phase, i.e. when under pressure is applied within the housing and blood is drawn into the flexible tubular membrane 102, more blood will be drawn into the flexible tubular membrane 102 via the first socket 117 than through the second socket 118. However, during the ejection phase, i.e. when overpressure is applied to the interior of the housing and blood is ejected from the flexible tubular membrane, approximately equal volumes of blood will be pushed through the first socket and the second socket. This results in a net circulation of blood through the flexible tubular membrane 102 over a succession of pumping cycles.

More in particular, the angled orientation of the second lumen branch 118 relative to the mutually aligned first lumen branch 117 and single-lumen portion 107 causes a pressure reduction due to flow through the first lumen branch 117 and single-lumen portion 107 to counteract inflow from the single-lumen portion 107 into the second lumen branch 118 in the aspiration phase and to promote inflow out of the second lumen branch 118 into the single-lumen portion 107 during the expulsion phase. This effect is particularly effective for achieving a net circulation through the flexible tubular membrane 102 over a succession of pumping cycles.

In the examples shown in FIGS. 5 and 6, the second lumen branch 218, 318 is composed of a first section 223, 323 branching off from the single-lumen portion 207, 307 at an obtuse angle $\alpha$ and a second section 224, 324 spaced from the single-lumen portion 207, 307, connected to the flexible tubular membrane 202, 302 and oriented more transversely to the single-lumen portion 207, 307 than the first section 223, 323 in order to improve the net circulation of blood through the flexible tubular member 202, 302. Preferably, the obtuse angle $\alpha$ enclosed between the single-lumen portion and the first section of the second lumen branch is at least a or larger than $\alpha_p$, $\alpha_p$ being in order of increasing preference 125°, 130° resp. 135°.

In the example shown in FIG. 5, the inner cross-section of the single-lumen portion 207 of the blood transfer conduit 203, the inner cross-section of the first lumen branch 217 and the inner cross-section of the first portion 223 of the second lumen branch 218 are substantially identical. In the example shown in FIG. 6, the inner cross-section of the single-lumen portion 307 of the blood transfer conduit 303 and the inner cross-section of the first lumen branch 317 are larger than the inner cross-section of the first portion 323 of the second lumen branch 318. This is also advantageous for enhancing net circulation through the flexible tubular member 302 over a succession of pumping cycles.

Figure 7:
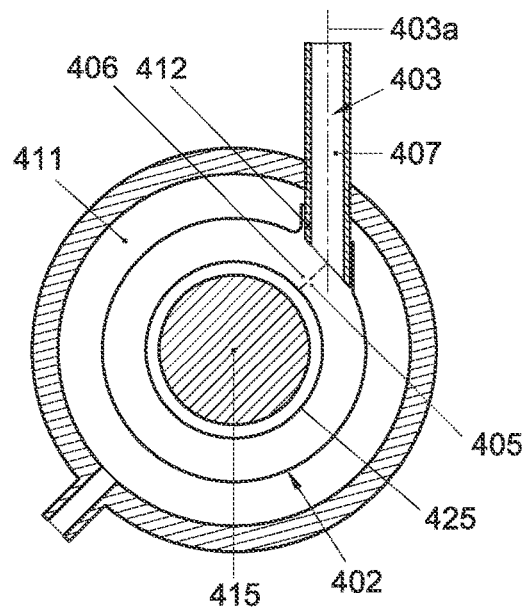

While some examples of pumping devices according to the invention have been described and shown, it will be clear to the skilled person, that within the framework of the invention as set forth in the claims, many other variants, obvious or not, are conceivable. For instance, in the example shown in FIG. 7, the flexible tubular membrane 402 is a loop-shaped membrane portion of which both ends 405, 406 are connected with each other and integrally formed with a part of the single-lumen portion 407 of the blood transfer conduit 403. The blood transfer conduit 403 is a single lumen, which may be curved, but is preferably straight for ease of manufacturing and for avoiding an increase of flow resistance. A socket 412 is included in the blood transfer conduit 403 and coupled to the portion of the blood transfer conduit 403 that is part of the membrane member. A centre line 403a is arranged tangentially to a ring-shape constituted by the loop-shaped flexible tubular membrane 402. The flexible tubular membrane 402 and the pressure transfer chamber 411 both extend around a centre 415 of the housing, so that also the pressure transfer chamber 411 has loop-shape. This off-centre arrangement of the blood transfer conduit 403 relative to the flexible tubular membrane 402 causes blood inflow into the loop-shaped flexible tubular membrane 402 to be directed in a circulating sense, while it has no or much less impact on the circulation of blood during outflow out of the closed ring-shaped portion of the flexible tubular membrane 402. Accordingly, also in this embodiment, in which the blood transfer conduit 403 consists of a single lumen, only, a net circulation of blood through the flexible tubular member 402 over a succession of pumping cycles is achieved when the pumping device is in operation.

The invention claimed is:

1. A pressure actuated single-lumen blood pumping device comprising:
   a housing having a wall bounding a pressure transfer chamber, the housing comprising a pressure transfer port for connection to a pressure source, the pressure transfer port communicating with the pressure transfer chamber for alternatingly transferring overpressure and under pressure from the pressure source to the pressure transfer chamber;
   a flexible tubular membrane in the pressure transfer chamber, the flexible tubular membrane having opposite ends and bounding a blood chamber; and
   a blood transfer conduit passing through the wall and having a single-lumen portion, a first lumen branch, and a second lumen branch, wherein the first and second lumen branches are in fluid communication with each other and the single-lumen portion at a common junction therebetween;
   wherein the blood transfer conduit has a first proximal end at an end of a first one of the lumen branches and a second proximal end at an end of a second one of the lumen branches, the first proximal end being coupled to a first one of the ends of the flexible tubular membrane and the second proximal end being coupled to a second one of the ends of the flexible tubular membrane.

2. The pumping device according to claim 1, wherein the flexible tubular membrane has a curved shape.

3. The pumping device according to claim 2, wherein the flexible tubular membrane constitutes at least sector of a circular ring-shape and wherein at least the single-lumen portion of the blood transfer conduit is arranged tangential to the flexible tubular membrane.

4. The pumping device according to claim 1, wherein the single-lumen portion of the blood transfer conduit is in line with a symmetry plane of the housing and wherein the lumen branches of the blood transfer conduit are oriented obliquely and located mirror symmetrical relative to the single-lumen portion of the blood transfer conduit.

5. The pumping device according to claim 1, wherein the single-lumen portion of the blood transfer conduit is in line with the first branch and wherein the second lumen branch joins the single-lumen portion and the first lumen branch in an orientation with a directional component transverse to the single-lumen portion and the first lumen branch.

6. The pumping device according to claim 5, wherein the single-lumen portion of the blood transfer conduit is in line with the first end of the tubular membrane.

7. The pumping device according to claim 5, wherein the second lumen branch comprises a first section branching off from the single-lumen portion at an obtuse angle and a second section spaced from the single-lumen portion, connected to the flexible tubular membrane and oriented more transversely to the single-lumen portion than said first section.

8. The pumping device according to claim 7, wherein said first section has a smaller inner cross-section than an inner cross-section of said second section.

9. The pumping device according to claim 5, wherein the single-lumen portion has a larger cross-section than each of the inner cross-sections of the first and second lumen branches.

10. The pumping device according to claim 1, wherein centre-lines of the lumen branches enclose an angle of 90°.

11. The pumping device according to claim 1, wherein the curved flexible tubular membrane is integral with a section of the single-lumen portion of the blood transfer conduit, said section of the single-lumen portion of the blood transfer conduit being connected to a socket through which the blood transfer conduit extends.

12. The pumping device according to claim 1, wherein the pressure transfer chamber and the flexible tubular membrane are curved around a common central area.

13. The pumping device according to claim 1, wherein the housing is hermetically sealed.

14. The pumping device according to claim 1, further comprising a catheter or tube having a lumen communicating with the blood transfer conduit.

15. The pumping device according to claim 1, wherein said lumen branches are entirely enclosed within the wall bounding the pressure transfer chamber.

16. The pumping device according to claim 1, wherein said lumen branches join with said single lumen portion within the pressure transfer chamber.

17. The pumping device according to claim 1, wherein a portion of the flexible tubular membrane is attached to the housing.

18. A pressure actuated single-lumen blood pumping device comprising:
   a housing having a wall bounding a pressure transfer chamber, the housing comprising a pressure transfer port for connection to a pressure source, the pressure transfer port communicating with the pressure transfer chamber for alternatingly transferring overpressure and under pressure from the pressure source to the pressure transfer chamber;
   a flexible tubular membrane in the pressure transfer chamber, the flexible tubular membrane having opposite ends and bounding a blood chamber; and
   a blood transfer conduit passing through the wall and having a single-lumen portion branching into lumen branches at a junction of the single lumen portion and the lumen branches;
   wherein the blood transfer conduit has a first proximal end at an end of a first one of the lumen branches and a second proximal end at an end of a second one of the lumen branches, the first proximal end being coupled to a first one of the ends of the flexible tubular membrane and the second proximal end being coupled to a second one of the ends of the flexible tubular membrane,
   wherein the opposite ends of the flexible tubular membrane are each configured to allow a fluid to flow into the flexible tubular membrane when the pressure transfer chamber is under negative pressure and to flow out of the flexible tubular membrane when the pressure transfer chamber is under positive pressure.

* * * * *

UNITED STATES PATENT AND TRADEMARK OFFICE
CERTIFICATE OF CORRECTION

| | | |
|---|---|---|
| PATENT NO. | : 9,636,442 B2 | |
| APPLICATION NO. | : 13/743510 | |
| DATED | : May 2, 2017 | |
| INVENTOR(S) | : Yoram Karmon | |

It is certified that error appears in the above-identified patent and that said Letters Patent is hereby corrected as shown below:

In the Claims

In Column number 9, Line number 58, being Line 3 of Claim 5, please delete "with the first branch" and insert therefor --with the first lumen branch--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*